United States Patent [19]

Lares et al.

[11] 4,198,754
[45] Apr. 22, 1980

[54] DENTAL TURBINE SPINDLE ASSEMBLY

[76] Inventors: Joseph P. Lares, 111 Wellesley Crescent, Redwood City, Calif. 94062; Albert J. Lares, 351 Grove Dr., Portola Valley, Calif. 94025

[21] Appl. No.: 946,028

[22] Filed: Sep. 26, 1978

Related U.S. Application Data

[63] Continuation of Ser. No. 777,438, Mar. 14, 1977, abandoned.

[51] Int. Cl.[2] ............................................. A61C 1/12
[52] U.S. Cl. ................................ 433/129; 433/132
[58] Field of Search ............................ 32/27; 415/503

[56] References Cited

U.S. PATENT DOCUMENTS

| | | | |
|---|---|---|---|
| 3,324,553 | 6/1967 | Borden | 32/27 |
| 3,325,899 | 6/1967 | Staunt | 32/27 |
| 3,400,459 | 9/1968 | Stemler | 32/26 |
| 3,731,384 | 5/1973 | Brooks et al. | 32/27 |
| 3,871,097 | 3/1975 | Melde | 32/27 |
| 3,893,242 | 7/1975 | Lieb et al. | 32/27 |

FOREIGN PATENT DOCUMENTS

643140  9/1950  United Kingdom ................... 32/26

Primary Examiner—Louis G. Mancene
Assistant Examiner—John J. Wilson
Attorney, Agent, or Firm—Lothrop & West

[57] ABSTRACT

A dental turbine spindle assembly has a housing in which a pair of bearing supports are disposed concentric with an axis. A pair of bearings are disposed on the supports. A hollow spindle concentric with the axis is carried in a portion of the bearings and at one end projects through an opening in the housing. The projecting portion of the spindle is conical, is split and is threaded. A nut on the projecting portion is conical and is threaded to engage the spindle and has a circular portion partly disposed within a portion of a bearing. There is a wrench-receiving contour at the other end of the spindle accessible through an aperture in the housing.

2 Claims, 3 Drawing Figures

U.S. Patent    Apr. 22, 1980    4,198,754
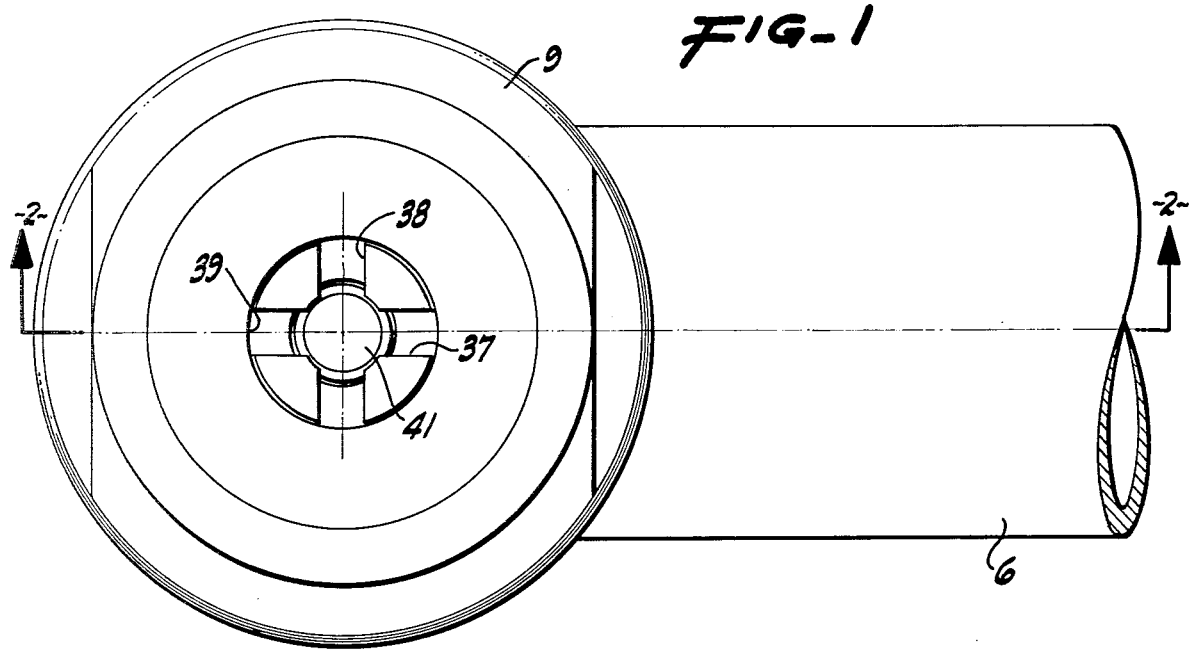
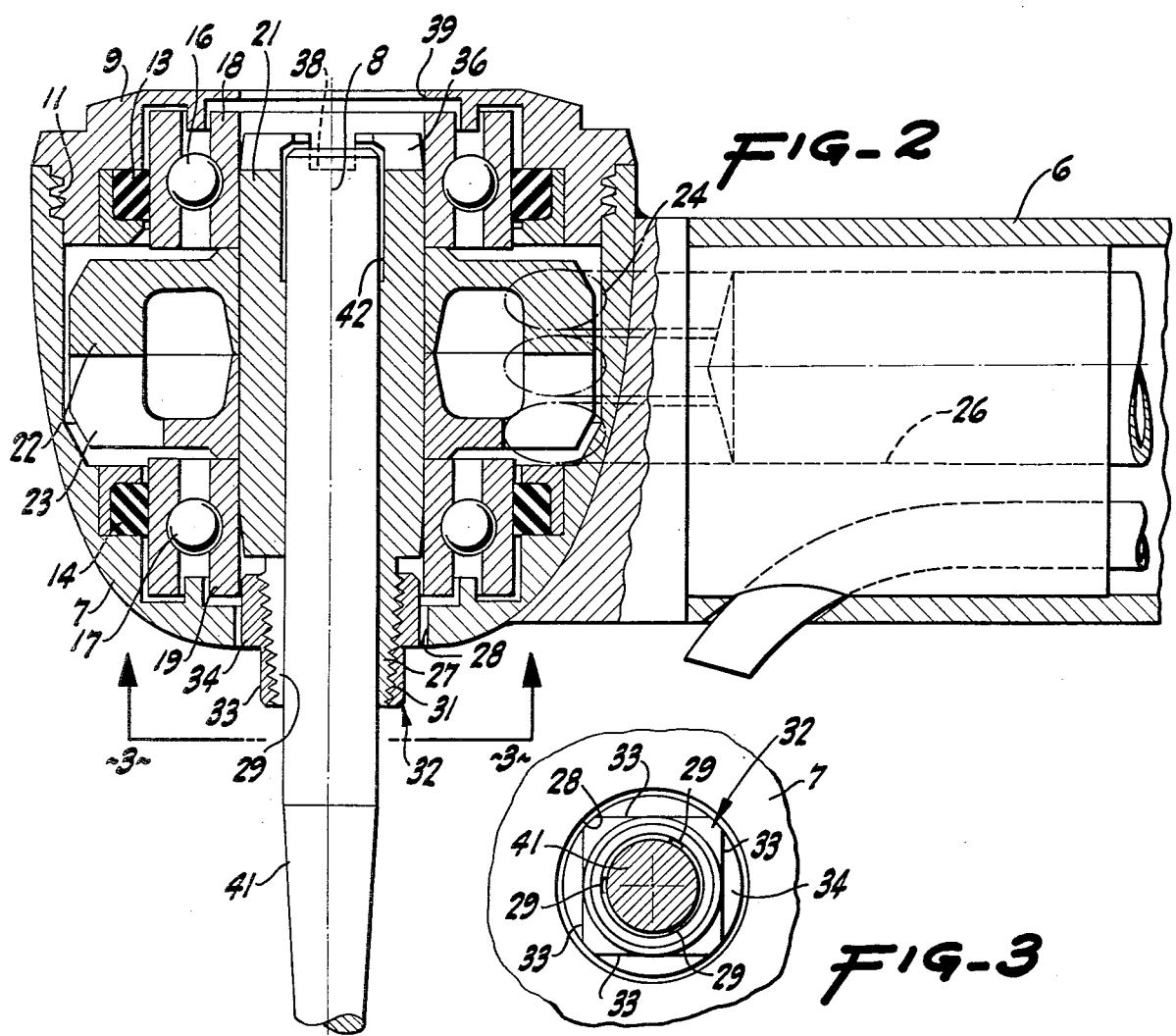

4,198,754

DENTAL TURBINE SPINDLE ASSEMBLY

CROSS-REFERENCES TO RELATED APPLICATIONS, IF ANY

This is a continuation of application Ser. No. 777,438, filed Mar. 14, 1977 and now abandoned.

The present applicants have filed a separate application entitled Dental Handpiece, Ser. No. 712,888, also relating to a turbine driven dental handpiece.

BRIEF SUMMARY OF THE INVENTION

In the above-noted related application there is shown a dental handpiece embodying a high-speed driving turbine. The arrangement of the turbine rotor support and of the means for holding a dental tool is comprised of a number of pieces. In the present instance there is a reduction in the number of pieces, partly for manufacturing reasons and partly to afford an improved support for the turbine rotor and for the dental tool itself. The present arrangement includes a construction in which a part of the mechanism for holding the dental tool in the spindle is at least in part housed within the main turbine housing.

BRIEF DESCRIPTION OF THE SEVERAL VIEWS OF THE DRAWING

FIG. 1 is a plan of a dental turbine spindle assembly according to the invention.

FIG. 2 is a cross-section, the plane of which is indicated by the line 2—2 of FIG. 1.

FIG. 3 is a detailed view from below taken on the line 3—3 of FIG. 2 and showing one end aspect of the mechanism.

DETAILED DESCRIPTION

In the construction of high-speed dental turbines it is necessary to keep the housing or enclosure as small as possible in order not to interfere with the dental work, yet the housing must be capacious and rigid enough to support the relatively high-speed rotor of the turbine mechanism. At the same time, the axial dimension of the turbine housing must be closely controlled, partly to keep it small enough not to interfere with dental operations, but also to make sure that the customary tools are properly located, supported and operated.

For this reason there has heretofore been provided a high-speed turbine housing included as part of a dental handpiece. In the known arrangement the turbine is mounted on a spindle which extends entirely through and projects from the housing and contains within it a sleeve having a threaded engagement with the spindle. The sleeve also has a tapered portion interengaging with a tapered portion of the spindle to serve as a grip for an inserted dental tool. While this arrangement is entirely satisfactory for many purposes, it requires expensive machining, several parts, and is not always as stiff and rigid as might be desired for very high-speed rotor operation.

It is therefore an object of this invention to provide a substantially improved dental turbine spindle arrangement which reduces the complexity of the mechanism, affords improved operation and does not increase external dimensions of the device.

In one form in which the invention is embodied, as shown in the accompanying figures, there is a dental handpiece shank 6 of customary nature and as shown in the mentioned application. The shank merges with a housing 7 symmetrical about an axis 8. The housing has a generally curved configuration of a minimum compass. Functioning as part of the housing, but made as a separate piece, is a housing cap 9 engageable with the rest of the housing by means of threads 11. When the two parts are fastened together there is in effect a single housing. Within the housing so formed, there are bearing supports 13 and 14. These preferably are elastomeric rings seated within the housing and affording resilient support. On the supports are situated ball bearings 16 and 17 concentric with the axis 8 and spaced apart a maximum distance within the housing.

In engagement with the inner races 18 and 19 of the bearings 16 and 17, but only extending part way into each inner race, is a hollow spindle 21. It has been found that it is not essential for the spindle to extend entirely through the inner bearing races 18 and 19 in order to be adequately supported and centered. The relatively short spindle not only reduces the weight and improves the balance of a principal rotating part but allows room for additional construction. Fast on the outside of the spindle are mounted a pair of complementary turbine rotors 22 and 23, as described in the above-identified application. These complementary rotors are fed with pressure air through inlet ports 24 and exhaust through housing openings and through the hollow interior 26 of the handpiece handle 6. The net result is that the turbine runners 22 and 23 or rotors are revolved simultaneously with each other and with the hollow spindle 21, the runners having a tight press fit on the spindle.

At one end the spindle is necked down to provide a conical portion 27 extending along the axis and projecting from the housing through an opening 28 in the lower end thereof. The spindle portion 27 also is provided with a number, usually three, of axially extending splits 29 and is provided with exterior threads 31. This portion 27 of the spindle is sufficiently resilient so that the fingers provided between the splits 29 can be moved toward and away from each other small amounts in a direction normal to the axis 8.

To take advantage of this fact, there is provided on this portion of the spindle a nut 32, the projecting portion of which has flats 33 in order to receive a wrench. The remaining portion 34 of the nut is circular-cylindrical so a easily to pass into the opening 28 and likewise to extend inwardly into the interior of the inner race 19, thus advantageously utilizing the space made available by the short spindle 21. The dimensions are such that when the nut 32 is initially started on the threads 31, there is no deflection of the fingers or intervening portions of the end of the spindle; but when the nut is advanced along the conical portion thereof, the fingers of the spindle between the splits 29 are directed toward each other and afford a gripping action. Both the steeply conical portion 27 and the threads 31 act in concert and supplement each other to provide an excellent gripping action. The circular portion 34 of the nut fills the opening 28 closely to allow clearance, yet to inhibit entrance of debris.

The other portion of the spindle at its upper, slightly inturned end is formed with a wrench-receiving configuration 36 usually afforded by a pair of cross slots 37 and 38 that are disposed just adjacent an aperture 39 concentric with the axis 8 and in the other end of the housing, specifically within the cover 9 thereof. The aperture 39 is large enough so that a wrench can be introduced therethrough to engage the wrench-receiving portion 36.

For customary use the spindle is supplied with any recognized form of dental tool 41 inserted through the lower end of the spindle when the nut 32 is loose. The tool shank extends almost all the way through the spindle and to a position adjacent the wrench-receiving portion 36 thereof but is stopped by the inturned end of the spindle. When the dental tool has been so positioned, the nut 32 is tightened with a suitable tool, the spindle being restrained against rotation by another tool in engagement with the portion 36.

With this arrangement the tool 41 can easily be clamped in position or, by a reverse operation, can be removed. In any event, when the tool is gripped in position, it is firmly supported by a portion of its length in the hollow spindle, although the upper portion of the spindle has a relief 42 so that the end of the tool 41 has some clearance. The tool thus is supported primarily by the central portion only of the spindle 21. Since the spindle is somewhat shorter than usual and since the tool is gripped only adjacent the projecting part of the spindle, the driving force is transmitted almost directly in a radial direction from the turbines 22 and 23 through the spindle to the active end of the tool, and much of the remaining structure is not put under any torque restraint of any substantial nature.

For the reason that much of the spindle weight is located near the center of the rotor, any rocking couple due to unbalance is reduced. Consequently, at ultra-high speed, the mechanism does not produce nearly as much vibration or resulting sound at intermediate speeds as has heretofore been encountered. Furthermore, since portions of each of the bearing races 18 and 19 are free to yield slightly during high speed operation, the bearing life is substantially increased over previous experience. In addition, since the hollow spindle 21 is of one piece, it is not only more rigid than heretofore, but more easily keeps concentric with its intended rotational axis, so that its rotation about that axis is more nearly true than heretofore.

In general there is provided by the presently disclosed dental turbine spindle assembly an arrangement which is a substantial improvement over previously known spindle arrangements and one in which the operating characteristics are improved, the manufacturing cost and complexity are reduced, and an improved operation is attained with fewer, less expensive parts.

We claim:

1. A dental turbine spindle assembly comprising a housing having an opening therein; means forming elastomeric bearing supports in said housing; bearings in said housing supported entirely on said bearing supports concentric with and spaced apart along an axis; a hollow cylindrical spindle portion in said housing directly engaging only a portion of the interior axial length of said bearings, extending along said axis and having an externally threaded end portion of reduced diameter projecting through said opening; a turbine runner directly mounted on said spindle between said bearings; axially extending slits in said end portion of said spindle dividing said end portion of said spindle into separate jaws directly engageable with a dental tool within said spindle; and an internally threaded nut partially within said housing and partially projecting through said opening and threadedly engaging said jaws, said hollow cylindrical spindle portion extending into only a portion of each of said bearings and a circular portion of said nut extending into a remaining portion of one of said bearings.

2. A dental turbine spindle as defined in claim 1 wherein said jaws are externally threaded, the threads thereof and the internal threads of said nut extending along an imaginary cone.

* * * * *